United States Patent [19]

Tóth et al.

[11] 4,086,246

[45] Apr. 25, 1978

[54] PROCESS FOR THE PREPARATION OF CARBAMATE DERIVATIVES

[75] Inventors: Geza Tóth; István Tóth; Tibor Montay, all of Budapest, Hungary

[73] Assignee: Chinoin Gyogyszer es Vegyeszeti Termekek Gyara, Budapest, Hungary

[21] Appl. No.: 682,033

[22] Filed: Apr. 30, 1976

[30] Foreign Application Priority Data

May 6, 1975 Hungary .............................. CI 1572

[51] Int. Cl.² .................. C07D 317/24; C07D 307/87
[52] U.S. Cl. .................. 260/340.9 R; 260/346.22; 548/306; 560/29; 560/31; 560/32; 560/115; 560/132
[58] Field of Search ............ 260/309.2, 553 A, 553 B, 260/553 D, 553 C, 553 R, 482 C, 471 C, 463, 340.9, 346.2 R, 397.7 D, 306.8 R

[56] References Cited

U.S. PATENT DOCUMENTS

| | | | |
|---|---|---|---|
| 1,307,570 | 6/1919 | Winkel | 260/553 C |
| 2,047,664 | 7/1936 | Barrett et al. | 260/463 |
| 2,189,205 | 2/1940 | Grether et al. | 260/463 |
| 2,380,130 | 7/1945 | Valentine | 260/463 |
| 2,745,874 | 5/1956 | Schetty et al. | 260/553 C |
| 2,758,975 | 8/1956 | Cottle et al. | 260/463 |
| 2,806,062 | 9/1957 | Gehauf et al. | 260/553 C |
| 2,936,322 | 5/1960 | Pfanstiel et al. | 260/553 C |
| 3,214,468 | 10/1965 | Frick et al. | 260/553 C |
| 3,673,210 | 6/1972 | Daum et al. | 260/309.2 |
| 3,773,781 | 11/1973 | Carlson et al. | 260/309 |
| 3,867,428 | 2/1975 | Kiefer et al. | 260/346.2 R |
| 3,920,829 | 11/1975 | Rohr et al. | 260/471 C |

FOREIGN PATENT DOCUMENTS

1,523,597 3/1968 France .............................. 260/309.2

*Primary Examiner*—Natalie Trousof
*Attorney, Agent, or Firm*—Karl F. Ross

[57] ABSTRACT

A process for the preparation of a compound of the formula:

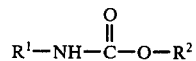

wherein $R^1$ is alkyl, alkyl substituted by halogen, alkyl substituted by alkoxy, aryl, aryl substituted by halogen, aryl substituted by alkyl, aryl substituted by alkoxy, aralkyl, aralkyl substituted by alkoxy, cycloalkyl, cycloalkyl substituted by halogen, cycloalkyl substituted by alkyl or cycloalkyl substituted by alkoxy, and $R^2$ is an aromatic group, an aromatic group substituted by alkyl, an aromatic group substituted by halogen, an aromatic group substituted by alkoxy, a heteroaromatic group, a heteroaromatic group substituted by alkyl, a heteroaromatic group substituted by halogen, or a heteroaromatic group substituted by alkoxy, by the reaction of phosgene with a phenol of the formula:

$R^2$-OH and further by the reaction of a primary amine of the formula:

$R'$—$NH_2$, reacting all three of the abovementioned reactants solution in a common water-immiscible organic solvent in the same reaction vessel at the same time in the presence of an acid binding agent to yield the compound of formula

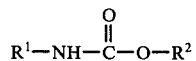

1 Claim, No Drawings

PROCESS FOR THE PREPARATION OF CARBAMATE DERIVATIVES

This invention relates to the substitution of phenolic hydroxy groups in organic compounds by an alkyl-, cycloalkyl-, aralkyl-, or aryl-carbamoyl group, which comprises introducing phosgene into a solution containing an organic compound bearing a phenolic hydroxy group and a primary alkylamine, cycloalkylamine, arylamine or aralkylamine, preferably in the presence of an acid binding agent.

The compounds prepared according to the present invention are useful in organic chemistry as pesticides.

The following compounds prepared according to the present invention are of outstanding importance: 1-methyl-2-[1,3-dioxolane-2-yl]-phenyl-N-methyl-carbamate as a pesticide.

According to the state of prior art these compounds were generally prepared by reacting a compound containing a phenolic hydroxy group with the corresponding isocyanate or reacting the corresponding urethane with an amine. According to a known process a compound containing a phenolic hydroxy group is reacted with phosgene and the chlorocarbonyl derivative thus obtained is reacted with an amine [e.g. German Patent No. 1,745,784]. According to another method the amine is reacted with phosgene and the carbaminic acid chloride thus obtained or rather the isocyanate formed when the latter compound is reacted with a phenol. Such a solution is mentioned in the description of Hungarian Patent Specification No. 153,303 without disclosing any reaction conditions.

The most commonly used reactants are the isocyanates. These methods require the preparation of an isocyanate by reacting the amine and phosgene, potassium cyanate or dimethylsulphate, acetic anhydride and sodium azide, sodium acetamide and thionyl chloride, etc.

There are several known methods for the preparation of methyl isocyanate or other isocyanates from phosgene and the corresponding amine. This reaction may be carried out by reacting the primary amine in vapor phase with phosgene and converting the carbamoyl chloride thus obtained into isocyanate by splitting off hydrochloric acid.

A further known method comprises the reaction of potassium cyanate and dialkylsulphate [Schotta and Lorenz]; the yields amount to 50–55%. It is further reported that methylisocyanate may be prepared by the reaction of acetic anhydride and sodium azide [U.S. Pat. No. 2,544,709]. This reaction is however expensive and complicated, since acid halides or acid anhydrides are treated in a solvent with alkali azide or alkaline earth metal azide, at 0°–45° C the azide is decomposed with water and the isocyanate is subjected to fractional distillation.

It is known furthermore that on reacting phosgene with primary amines or secondary amines the corresponding symmetrical urea derivatives are obtained in very good yields [H.W.8, pages 117, 120–123 and 154–157].

The safety measures ordered for the elimination of these reactions are partly due to the aforesaid. In every case, whenever phosgene is not used in a very large excess there is a possibility for the formation the diurea derivative and consequently the compounds can no more be converted into the isocyanate.

Probably the above reactions are partly responsible for the fact that the yields of the published procedures are generally far below the desired value.

The present invention is based on the surprising recognition that on introducing phosgene into a solution which contains an organic compound comprising a phenolic hydroxy group and a primary amine, the carbamate is produced in a single step.

According to a preferred embodiment of our process the reactants (namely the phenol and amine components) and the phosgene in parallel are added to the reaction mixture containing the solvent.

In order to achieve the desired results, it is essential to add an acid binding agent to the reaction mixture at a suitable point of time. The acid binding agent may be applied from the beginning of the reaction or at a later state of the addition of the reactants.

One may proceed preferably by using alkali hydroxides, alkali carbonates or alkaline earth metal carbonates for this purpose. The said acid binding agents are preferably added continuously to the reaction mixture. According to a particularly preferred embodiment of our process, the acid binding agent is added so as to form as heterogenous phase which separates from the organic solvent layer. Organic acid binding agents or ammonium carbonate may be used as well.

The acid binding agent may be added as a solid substance or as a solution (e.g. aqueous solution).

As solvent preferably halogenated hydrocarbons (e.g. dichloroethane or dichlorobenzene) may be used. Water-immiscible organic solvents (e.g. toluene) may be used too.

The process of the present invention is particularly suitable for the preparation of compounds of the formula

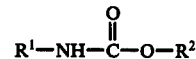

wherein
R¹ is alkyl, alkyl substituted by halogen, alkyl substituted by alkoxy, aryl, aryl substituted by halogen, aryl substituted by alkyl, aryl substituted by alkoxy, aralkyl, aralkyl substituted by halogen, aralkyl substituted by alkyl, aralkyl substituted by alkoxy, cycloalkyl substituted by halogen, cycloalkyl substituted by alkyl or cycloalkyl substituted by alkoxy, and
R² is an aromatic group, an aromatic group substituted by alkyl, an aromatic group substituted by halogen, an aromatic group substituted by alkoxy, a heteroaromatic group, a heteroaromatic group substituted by alkyl, a heteroaromatic group substituted by halogen, or a heteroaromatic group substituted by alkoxy, by the reaction of phosgene with a phenol of the formula:

and further by reaction of a primary amine of the formula:

the improvement by reacting all three of the abovementioned reactant solution in a common water-immiscible organic solvent in the same reaction vessel at the same time in the presence of an acid binding agent to yield the compound of formula $$R^1-NH-\overset{O}{\underset{\|}{C}}-O-R^2$$

The process of the present invention provides a highly advantageous method for the preparation of alkyl-1-butyl-carbamoyl-benzimidazole-2-carbamates (1-n-butyl-carbamoyl-benzimidazole-2-carbaminic acid alkyl esters).

Further details of the present invention are to be found in the Examples.

EXAMPLES:

1. Into a 1 liter glass equipped with a stirrer, reflux condenser, thermometer gas introducing tube and a dropping funnel 150 ml of tolune are added, whereupon a solution of 46.5 g (0.5 moles) of aniline and 70 ml of toluene is added dropwise at 0° C within an hour. In an other apparatus 80 g (0.48 moles) of 2-[1,3-dioxolane-2-yl]-1-hydroxy-benzene, 35 ml of toluene and 10 ml of triethylamine are admixed under stirring, whereupon the toluene solution is poured into the second apparatus under constant introduction of phosgene. The temperature of the reaction mixture is raised to 90°–92° C and it is stirred for 2 hours, while phosgene is continuously led into the reaction mixture. Thereafter nitrogen is led into the apparatus at 80° C for 2 hours. The reaction mixture is cooled to room temperature, stirred for 8 hours; the precipitated product is filtered off and washed successively with a small amounts of toluene and 60 ml of ethanol (0° C). Thus 124.5 g of 2-[1,3-dioxolane-2-yl]-phenyl-N-phenyl-carbamate are obtained.

The compounds of the formula I enumerated in Table I are prepared in an analoguous manner to the process of the preceding examples by using the corresponding starting materials.

What we claim is:

1. In a process for the preparation of a compound selected from the group which consists of:
    2-(1,3-dioxolane-2-yl)-phenyl-N-phenyl-carbamate;
    2-(1,3-dioxolane-2-yl)-phenyl-N-methyl-carbamate;
    2-(1,3-dioxolane-2-yl)-phenyl-N-3-chlorophenyl-carbamate;
    2-(1,3-dioxolane-2-yl)-phenyl-N-cyclohexyl-carbamate;
    2-(1,3-dioxolane-2-yl)-phenyl-N-3,4-dichlorophenyl-carbamate;
    2-(1,3-dioxolane-2-yl)-phenyl-N-4-chlorophenyl-carbamate;
    2,2-dimethyl-2,3-dihydro-benzofuran-7-yl-N-methyl-carbamate;
    3-methyl-phenyl-N-methyl-carbamate;
    2-chlorophenyl-N-methyl-carbamate; and
    4-isopropylphenyl-N-methyl-carbamate
by reaction of phosgene with a phenol of the formula:

$$R^2-OH$$

and further by the reaction of a primary amine of the formula:

$$R^1-NH_2$$

wherein $R^1$ is selected from the group which consists of methyl, cyclohexyl, phenyl, 3-chlorophenyl, 4-chlorophenyl, and 3,4-dichlorophenyl; and $R^2$ is selected from the group which consists of 2-(1,3-dioxolane-2-yl)-phenyl, 3-methylphenyl, 2-chlorophenyl, 4-isopropylphenyl, and (2,3-dihydro-2,2-dimethyl-benzofuran-7-yl); the improvement which comprises reacting all three of the abovementioned reactants in a common water-immiscible organic solvent in the same reaction vessel at the same time in the presence of an acid binding agent and with about a 1:1 molar ratio of the phenol to the primary amine to yield the desired product.

* * * * *